United States Patent [19]
Berman et al.

[11] Patent Number: 5,560,890
[45] Date of Patent: Oct. 1, 1996

[54] APPARATUS FOR GAS GLOW DISCHARGE

[75] Inventors: Charles H. Berman, East Windsor; Hartwell F. Calcote, Princeton, both of N.J.

[73] Assignee: Gas Research Institute, Chicago, Ill.

[21] Appl. No.: 420,985

[22] Filed: Apr. 10, 1995

Related U.S. Application Data

[63] Continuation-in-part of Ser. No. 98,736, Jul. 28, 1993, Pat. No. 5,405,514.

[51] Int. Cl.$^6$ .................................................. B01J 19/08
[52] U.S. Cl. ..................... 422/186.04; 422/168; 422/907
[58] Field of Search .............................. 422/186.04, 907, 422/168

[56] References Cited

U.S. PATENT DOCUMENTS

| | | | |
|---|---|---|---|
| 2,719,184 | 9/1955 | Kosbahn et al. | 260/679 |
| 2,787,730 | 4/1957 | Berghaus et al. | 315/111 |
| 2,799,640 | 7/1957 | Pevere et al. | 204/171 |
| 3,018,409 | 1/1962 | Berghaus et al. | 315/111 |
| 3,035,205 | 5/1962 | Berghaus et al. | 315/111 |
| 3,423,562 | 1/1969 | Jones et al. | 219/121 |
| 3,483,107 | 12/1969 | Schwarz | 204/162 |
| 3,623,145 | 11/1971 | Gregg | 331/94.5 |
| 3,681,639 | 8/1972 | Kamel et al. | 313/151 |
| 3,704,428 | 11/1972 | Barry et al. | 331/94.5 |
| 3,781,713 | 12/1973 | Barry et al. | 331/94.5 |
| 3,982,209 | 9/1976 | Sutton et al. | 331/94.5 |
| 4,031,428 | 6/1977 | Tokudome et al. | 315/111 |
| 4,335,462 | 6/1982 | Hasson et al. | 372/85 |
| 4,604,752 | 8/1986 | Sequin et al. | 372/29 |
| 4,830,492 | 5/1989 | Ko | 356/313 |
| 4,877,589 | 10/1989 | O'Hare | 204/178 |
| 4,963,792 | 10/1990 | Parker | 315/58 |
| 4,967,118 | 10/1990 | Urataki et al. | 315/56 |
| 4,970,425 | 11/1990 | Barakitis | 313/39 |

OTHER PUBLICATIONS

Berman, C. H., Calcote, H. F. and Gill, R. J., Supersonic Combustion Enhancement by a Nonequilibrium Plasma Jet, Contract No. NAS1–18404, Final Report, AeroChem TP–467, (Aug. 1987).
Fan, H. Y., The Transition from Glow to Arc, Phys.Rev., 55, 769, (1939) No month available.
Wiener, H. and Burton, M., Decomposition of Methane in an Electrical Discharge, J.Am.Chem.Soc., 75, 5815 (1953).
Schoch, E. P., et al., Acetylene from Hydrocarbons, University of Texas Publication No. 5011, (Jun. 1950).
Pettyjohn, E. S., German Use of Natural Gas, A.G.A. Natl. Gas Dept. Proc., 33, (1946) No month available.
GRI Final Report entitled "Conditioning of Natural Gas Using a Nonequilibrium Glow Discharge", Gas Research Institute, Chicago, IL 60631, (Oct. 1990–Oct. 1991). No Month Available.
Jahn, Robert J., Physics of Electric Propulsion, pp. 116–121, 140–141, McGraw–Hill Series in Missle and Space Technology, McGraw–Hill Book Company, New York, N.Y., (1968) No Month available.
Berman et al., Supersonic Combustion by a Nonequilibrium Plasma Jet, Aug. 1987, pp. 1–25.
Berman et al., Conditioning of Natural Gas Using a Nonequilibrium Glow Discharge, GRI Report, Oct. 1991, pp. 1–11.

*Primary Examiner*—Kathryn Gorgos
*Attorney, Agent, or Firm*—Speckman, Pauley & Fejer

[57] ABSTRACT

An apparatus for glow discharge at pressures of atmospheric and above stabilized between two electrodes spaced apart greater than 3 mm by a swirling gas path. The passage of a reactant gas in the swirling gas stream may be utilized for highly efficient chemical reactions and heating of the gas stream. The simple and compact apparatus for atmospheric pressure glow discharge is suitable for chemical conversion of hydrocarbon gases into higher molecular weight products of greater value, for pretreating combustible hydrocarbon gases for enhanced combustion and for production of intense white light.

23 Claims, 4 Drawing Sheets

APPARATUS FOR GAS GLOW DISCHARGE

CROSS REFERENCE TO RELATED APPLICATION

This application is a continuation-in-part of application Ser. No. 08/098,736 filed Jul. 28, 1993, now U.S. Pat. No. 5,405,514.

BACKGROUND OF THE INVENTION

1. Field of the Invention

This invention relates to a process and apparatus for gas glow discharge, particularly hydrocarbon gas glow discharges at about atmospheric pressure with high conversion of methane to acetylene and efficient conversion of electrical energy into chemical conversions. This process may be used for high efficiency transfer of energy in the conduct of chemical reactions, such as a pretreatment for hydrocarbon gases, such as natural gas, to provide increased flame radiation and stability upon combustion. The hydrocarbon gas glow discharge according to this invention provides a high intensity white light and high volume light source. The glow discharge according to this invention may also be used to activate non-hydrocarbon gases, such as hydrogen, nitrogen, oxygen, ammonia, or silanes in molecular form to produce the corresponding atoms, ions, or excited species, such as free radicals.

2. Description of Related Art

Low pressure gas glow discharges and apparatus for their production are known from a number of U.S. Patents, for example U.S. Pat. Nos.: 2,787,730; 3,018,409; 3,035,205; 3,423,562; 4,830,492; 4,963,792; and 4,967,118. Glow discharge ignitors are known, for example, from U.S. Pat. Nos. 3,681,639 and 4,970,425.

Glow discharges are usually operable at subatmospheric pressure, typically less than about 20 Torr. When the pressure is increased, the glow discharge becomes an arc discharge. The two types of discharge are distinguished by their electrical characteristics and their mode of operation. A glow discharge operates at high voltage and low currents, while an arc discharge operates at low voltage and high currents. As the current is increased for a glow discharge, the discharge tends to cover more and more of the available cathode area until at some point the current density exceeds a critical value and the discharge suddenly becomes an arc. When this occurs, there is an abrupt drop in voltage and an increase in current. In the glow discharge, electrons are produced in the gas phase by ionization of neutral species by electrons accelerated by the electric field; in the arc discharge, the electrons are produced by copious emission of electrons from a hot cathode. Generally, the electrodes are not consumed in a glow discharge; while in an arc discharge, the cathode is consumed and must be replaced frequently.

Atmospheric pressure glow discharges in hydrogen have been described by Berman, C. H., Calcote, H. F. and Gill, R. J., Supersonic Combustion Enhancement by a Nonequilibrium Plasma Jet, Contract No. NAS1-18404, Final Report, AeroChem TP-467, (August 1987) and in air and hydrogen by Fan, H. Y., The Transition from Glow to Arc, Phys.Rev., 55, 769, (1939). In both of these cases, the electrode separation was very small, on the order of 1 mm. The observed discharges were identified as glow discharges because of the voltage/current relationship. However, in a normal glow discharge, the electrode spacing can be increased by increasing the applied voltage. In the above examples, this led to an arc discharge, so it may in fact be questioned as to whether a true glow discharge was observed.

Swirl has been used to stabilize arc discharges by moving the arc over the electrodes so they will not overheat or to spread the arc through gas flowing through the device. Jahn, Robert J., Physics of Electric Propulsion, pgs. 116–121, 140–141, McGraw-Hill Series in Missile and Space Technology, McGraw-Hill Book Company, New York, N.Y., (1968).

High power glow discharge lasers and apparatus for their production are known from a number of U.S. Patents, for example U.S. Pat. Nos.: 3,623,145; 3,704,428; 3,781,713; 3,982,209; 4,031,428; 4,335,462; and 4,604,752.

Production of acetylene from hydrocarbons by various methods is known: U.S. Pat. No. 2,719,184 teaching incomplete combustion with oxygen in a flame reaction; U.S. Pat. No. 2,799,640 teaching catalyzation by spark discharge; and U.S. Pat. No. 3,483,107 teaching utilization of radio frequency plasma jets. Laboratory scale electrical discharge conversion of methane to acetylene using a small spacing between electrodes and operated with very low flow rates has been described in Wiener, H. and Burton, M., Decomposition of Methane in an Electrical Discharge, J.Am. Chem. Soc., 75, 5815 (1953). Recycle of processed gases through an electrical discharge in the conversion of natural gas to acetylene has been described in Schoch, E. P., et al, Acetylene from Hydrocarbons, University of Texas Publication No. 5011, (June 1950). Pettyjohn, E. S., German Use of Natural Gas, A.G.A. Natl. Gas Dept. Proc., 33, (1946) describes an arc process

SUMMARY OF THE INVENTION

Glow discharges have many advantages over electric arcs for chemical conversions. Glow discharges do not consume the electrodes as do arcs. Glow discharges provide much higher energy efficiencies than arcs since glow discharges are nonequilibrium devices operated at much lower temperatures with ionization produced by electric field acceleration of electrons rather than by thermal ionization, thereby consuming much less heat capacity energy and greatly reducing energy loss due to radiation. Further, glow discharge devices are much simpler and more compact than arc discharge devices making the glow discharge devices much more readily integrated into associated apparatus.

Glow discharges normally have been considered low pressure discharges, operated at pressures of less than about 20 Torr. As the pressure is increased, the prior glow discharges have become a spark or arc. Prior nonequilibrium glow discharges have been limited due to the necessity of the electrodes being spaced no further apart than about 1 mm to maintain a stable glow discharge as atmospheric pressure is approached. This close electrode spacing limits the volume of the glow discharge and, thus, the flow volume of gas which may be treated in the glow discharge. The requirement for operation at subatmospheric vacuum pressures to obtain greater electrode spacing is not desirable due to the requirement of a substantial vacuum pump and of an enclosed subatmospheric pressure chamber and process gas pressure control.

It is an object of this invention to provide a method and apparatus for stable glow discharges at higher pressures than previously operable.

It is another object of this invention to provide a method and apparatus for high gas flow stable glow discharges at about atmospheric pressure.

Yet another object of this invention is to provide a method and apparatus for stable glow discharges at greater electrode spacings and at higher pressures than previously operable.

It is still another object of this invention to provide a method and apparatus for conducting chemical reactions by passing reactant gas or vapor through a glow discharge and transferring energy from the glow discharge to the reactant gas forming product gas.

It is an object of this invention to provide a method and apparatus for pretreating combustible hydrocarbon gas or vapor to produce higher molecular weight hydrocarbons, carbon soot and hydrogen by passing hydrocarbon gas, such as methane or natural gas, through a glow discharge at higher volume flow and higher pressure than prior glow discharges.

Still another object of this invention is to provide a method and apparatus for conduct of reactions of reactant gases, such as hydrogen, nitrogen and oxygen in molecular form to produce the corresponding atoms, ions or excited species.

Yet another object of this invention to provide a method and apparatus for conversion of gaseous molecules into reactive atoms and free radicals, such as $NH_3$ to produce $N\bullet$ and $NH_2\bullet$ and silane to produce $Si_x\bullet$ and $H\bullet$.

It is another object of this invention to provide a method and apparatus for creating an intense white light by passing hydrocarbon gas, such as methane or natural gas, through a glow discharge at higher pressure than prior glow discharges.

These and other objects and advantages of the invention are achieved by passing gas or vapor in a swirling pathway to form a vortex between two opposing electrodes within a glow discharge chamber, a first of the electrodes having an electric potential with respect to the second of the electrodes sufficiently different to maintain a glow discharge between the electrodes, and passing the gas or vapor through an exit port from the discharge chamber in or near one of the electrodes at the downstream end of the vortex. The swirling gas stabilizes the glow discharge permitting separation of the electrodes to distances of more than about 3 mm apart and operation of the glow discharge at pressures of up to several atmospheres. Greater separation of the electrodes allows much higher flow volumes of reactant gas to pass through a much larger glow discharge volume providing higher energy transfer for efficient conduct of chemical reactions, such as conversion of hydrocarbon gas to higher hydrocarbons, carbon and hydrogen. Operation of these types of glow discharges at higher pressures, such as atmospheric, greatly reduces energy and design requirements of the system. The small size, operation at about atmospheric pressure, and simplicity of operation of the apparatus of this invention permits its facile incorporation into other chemical systems and processes, such as pretreatment of combustible hydrocarbon gases in close association with a burner for enhancement of combustion, as a source of injection gases for spark ignition engines, or as a source of reactive gas, such as hydrogen, nitrogen or oxygen atoms obtained from the corresponding molecular gases to be used as chemical reactants.

BRIEF DESCRIPTION OF THE DRAWINGS

The above and further objects and advantages of this invention will become apparent upon reading the description of specific preferred embodiments with reference to the drawings, wherein.

DESCRIPTION OF PREFERRED EMBODIMENTS

The glow discharge according to this invention is generally conducted between two opposing electrodes within a glow discharge chamber. By the terminology chamber, as used in this description and claims, we do not mean to be limited to a closed chamber. Since the glow discharge may be operated at atmospheric pressures, there is not the requirement of a physical chamber for maintenance of very low subatmospheric pressures. When operating at about atmospheric pressures, chamber walls may have openings for passage of light created by the glow discharge, or the chamber may be created and defined by swirling gas without the requirement of physical walls. To aid in gas flow, at least some physical definition of a chamber is usually present, but it is a feature of this invention that a large portion of the chamber may be open to the atmosphere.

The electrodes may be of any suitable material as known to the art and may be cooled, if desired, by any means known to the art, such as by water or gas flow. Copper and brass are suitable electrode materials due to their high electrical conductivity and heat transfer coefficients, and stainless steel and nickel are suitable due to their high mechanical strength. The electrodes may be a wide variety of shapes and each electrode may be of a different shape, as will be specifically exemplified below. An electrode may be shaped as a flat disc, a partial cone, a wire, a sphere, and may have concave or convex face surfaces. One or both of the electrodes may define a gas entry port or a gas exit port. One of the electrodes is maintained at a higher positive electrical potential than the other electrode, the potential differential being sufficient to maintain a glow discharge between the electrodes. The potential differential is generally on the order of kilovolts, about 1 to about 5 kilovolts, but may be as low as 100 volts. A potential is applied between two electrodes, and one of the electrodes may be maintained at ground for safety reasons by means known to the art.

The glow discharge may be initiated by any suitable means known in the art. With the electrodes separated the desired distance for use in this invention, ignition may be achieved by using a vacuum pump to reduce the pressure to the point where ignition occurs easily and then raising the pressure to the desired operating pressure. The glow discharge may be initiated by igniting a low pressure air or nitrogen discharge, at less than about 0.1 atmosphere, and then adding the desired reactant gas and increasing the pressure to the desired pressure with flow of reactant gas and turning off the nitrogen flow. It is not necessary to have a flowing system or to use any particular gas for this type of ignition. The reduced pressure may be attained by a small mechanical pump when there is no flow through the system by reducing the pressure in a large volume and then connecting the large low pressure volume to the discharge chamber. The glow discharge may also be ignited by having at least one of the electrodes movable to reduce the electrode distance for ignition and then returning the electrode(s) to the desired operating distance. Likewise, a stationary or movable separate ignition electrode may be used. A supplementary electrical supply, such as a Tesla coil, may also be used to aid in ignition.

An important feature of this invention is the passage of gas or vapor in a swirling pathway between the two electrodes and passing the gas through an exit port in or near one of the electrodes, thereby forming a vortex of the swirling gas through the glow discharge between the electrodes and having its downstream end at or near the exit port. Introduction of the gas in a tangential or swirling manner in the region of the electrode opposing the exit port combined with the flowing exit of gas from the exit port creates the desired vortex of the swirling gas. The radially inward component of the swirling gas approaching the exit port also aids in the stability of the glow discharge by keeping the discharge centered, particularly between electrodes spaced more than about 3 mm apart. Electrode spacing of about 3 to about 200 mm is suitable for use in this invention, spacing about 5 to about 25 mm apart being preferred. Stability may also be improved by a ring, or other appropriate structure on the electrode opposing the gas exit port to aid in attachment of the base of the glow discharge to that electrode. While a stable glow discharge could be maintained for gas flows entering and exiting through opposed electrode gas ports, a much higher gas flow rate may be maintained with gas entering through tangential swirl tubes. Gas flow velocities of about 0.1 to about 10,000 meters per second may be used in this invention, about 1 to about 100 meters per second most frequently used, and about 10 to about 50 meters per second most preferred. The greater spacing of electrodes makes the requirements for their being parallel, which has been a problem in previous closely spaced electrode glow discharges, much less critical. The gas swirl moves the point of heating on an electrode surface to aid in preventing arcing. The swirling gas also provides enhanced energy transfer for chemical reaction in passage through the glow discharge. We observed that, except at the low pressures used to initiate the glow discharge, the swirling gas always tended to form a narrow cylindrical type volume, which is typical of high pressure discharges. Therefore, the only manner in which the discharge volume could be increased was by making it longer by increasing the electrode spacing. The larger discharge volume is also advantageous due to the increased amounts of electric power which can be delivered to the discharge.

The larger electrode spacing and the enhanced energy transfer achieved by the swirling gas action according to this invention makes possible much larger gas flows through the glow discharge for chemical reaction. Flow rates of about 4 to about 15 liters per minute were found to be practical with a chamber of 10 ml volume and an exit port of 4 mm diameter. A wide variety of chemical reactions utilizing energy from a glow discharge may be conducted by passage of gas through the glow discharge according to this invention. For example, hydrocarbon gas, selected from methane, ethane, propane and natural gas, which have been particularly recalcitrant to reaction, may be converted to more valuable compounds by the method of this invention. We have found, with electrodes 10 mm apart, high conversion of methane to acetylene, obtaining forty percent of the maximum possible conversion. We have also found high efficiency utilization of electrical energy into chemical change, on the order of over fifty percent. Non-hydrocarbon gases may be activated in a similar manner by passage through the glow discharge of this invention. Diatomic molecules, such as hydrogen, nitrogen and oxygen may be converted to the corresponding atoms, ions or excited species, and polyatomic molecules, such as ammonia and silane may be converted into reactive atoms and free radicals, such as $NH_3$ to produce N• and $NH_2$• and $SiH_4$ to produce $Si_x$• and H•.

The high conversion of methane to acetylene makes the process of this invention very attractive for pretreating hydrocarbon combustible gases or vapor prior to combustion to form products comprising higher hydrocarbons, hydrogen and carbon soot. Combustion of these products significantly enhances radiant energy output of a burner, enhances flame luminosity, stabilizes the flame and increases burning velocity, resulting in increased throughput capability. Methane pyrolysis with the supply of 45 kcal/mole methane results in hydrogen and acetylene with the ratio of hydrogen:acetylene of 3:1. Thus, the maximum possible concentration of acetylene in the product gases with the complete decomposition of methane is 25 percent. Prior attempts in the conversion of methane to acetylene have resulted in direct carbon formation which requires only 17.89 kcal/mole of methane. For burner applications, it is more desirable to form carbon in the flame from acetylene due to the ease of transport of acetylene as compared to carbon. According to the present invention, formation of high amounts of acetylene and hydrogen with some soot by pretreating combustible hydrocarbon gases at about atmospheric pressure provides an enhanced combustible gas for direct combustion. The atmospheric pressure gas glow discharge between widely spaced electrodes also very efficiently heats the gas stream providing preheated gas for combustion, utilizing much of the electrical energy to the discharge. The electrical energy not consumed in activating the reactants or transferred to the chamber walls is deposited in the gas to heat it. Operation of the glow discharge at about 0.5 to about 10 atmospheres, including atmospheric and higher pressures, and the simplicity of the apparatus allows the glow discharge to be incorporated into a burner, eliminating problems of soot transport.

Figure 3:
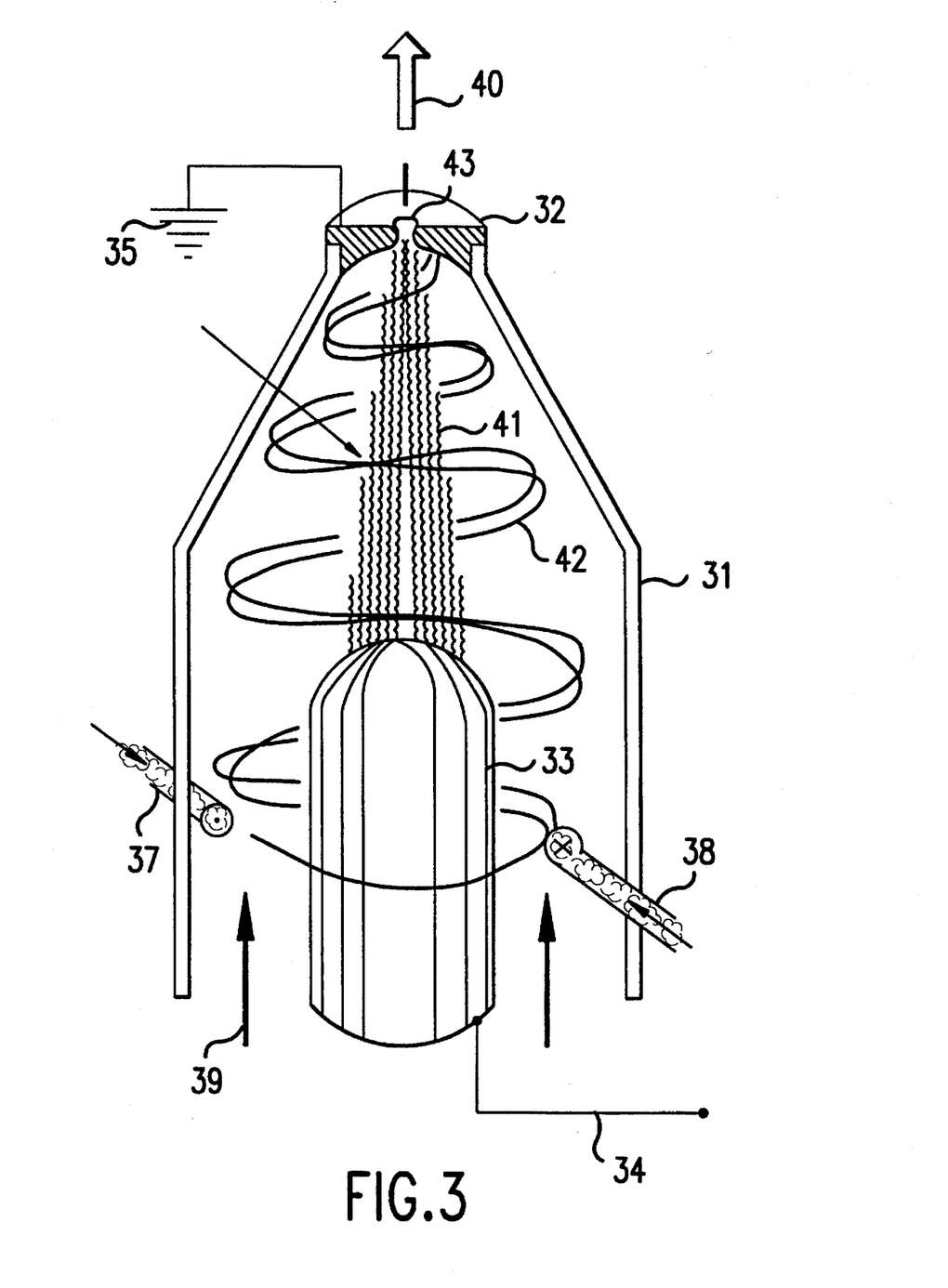
FIG. 3 is a cross-sectional view of another embodiment of an atmospheric pressure gas glow discharge chamber according to this invention suitable for pretreatment of combustible gases.

FIG. 3 schematically shows one embodiment of a suitable atmospheric glow discharge device for incorporation into a burner. Chamber wall 31 is cylindrical in its lower portion surrounding electrode 33 and is conically shaped in its upper portion to fit electrode 32. Electrode 33 is connected to DC power source 34, positive polarity, and electrode 32 is connected to ground 35 to maintain the desired voltage between the electrodes. Alternating current as well as direct current power can be used to sustain the glow discharges. Combustible gas is fed into the glow discharge chamber through swirl tubes 37 and 38, and additional combustible gas may be fed axially as shown by arrows 39. The gas passes in a swirling motion, shown by path 42, about and through glow discharge 41 and exits through exit port 43 in the center of electrode 32 as product stream 40. One manner of incorporation into a burner is to have the higher than atmospheric pressure glow discharge device shown in FIG. 3 surrounded by an annular oxidizer or air flow chamber and to burn the product gas directly passing from exit port 43. The same apparatus, in a similar manner, can provide reactive gases, such as hydrogen, nitrogen or oxygen atoms produced from the corresponding molecular gases passed through the glow discharge; or, an oxidizing gas can pass through the discharge port into a stream of fuel and ignite a flame.

The method and apparatus of this invention may also be used to create an intense white light by passing hydrocarbon gas or vapor in the swirling pathway between two electrodes. An intense white light is formed when passing pure hydrocarbon gas or smaller concentrations of about 3 to about 60 percent in a carrier gas, such as nitrogen, through the glow discharge. The greater separation distance of the electrodes provides a larger volume of the radiating source than previously obtainable. The white light emission fills a significantly larger volume than the discharge itself, and it is believed that the formation of small soot particles and their activation by the glow discharge renders them efficient radiators of the light. A luminous jet could also be formed by soot particles leaving through the exit jet. The swirling gas pattern also aids in preventing soot build-up on transparent portions of the glow discharge chamber. Operation of the glow discharge of the present invention at about atmospheric pressure also allows openings in the glow discharge chamber for passage of the light, making the intense light available for many uses. Operation of the glow discharge at 200 Watts with a natural gas flow produced a white light of intensity far greater than a 200 Watt light bulb.

Figure 1:
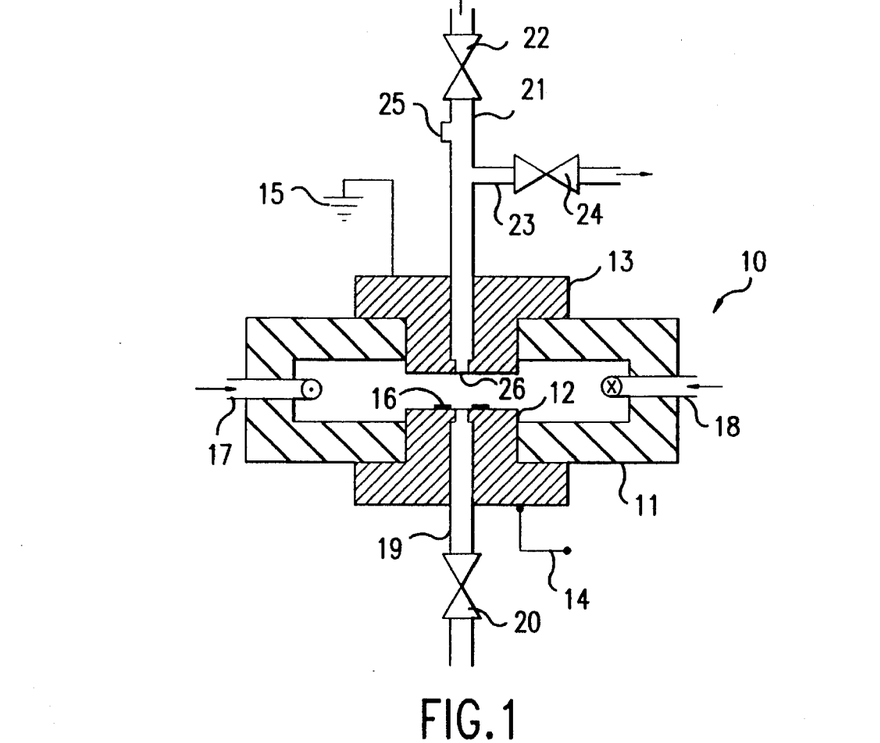
FIG. 1 is a cross-sectional view of one embodiment of a atmospheric pressure gas glow discharge chamber according to this invention.

In the specific embodiment shown in FIG. 1, glow discharge chamber 10 was formed with copper disc-shaped electrodes 12 and 13, 32 mm in diameter, spaced apart 10 mm by circular non-electrically conducting acrylic walls 11 with gas inlet swirl tubes 17 and 18. The electrode faces were flat and each of the electrodes had a central port of 4 mm inside diameter for introduction or outlet of gas. Ring 16 provided attachment for the base portion of the glow discharge to aid in stabilization of the discharge and to prevent it from wandering over the surface of electrode 12. Electrode 12 was connected to D.C. power supply 14 (positive polarity). Electrode 13 was connected to ground 15. Gas inlet tube 19, in communication with the central inlet port in electrode 12, was controlled by valve 20. Gas outlet tube 21, in communication with central exit port 26 in electrode 13, was controlled by valve 22. Vacuum tube 23, controlled by valve 24, provides communication with a vacuum pump (Not shown). Gas sampling tube 25 provides communication from gas outlet tube 21 to any desired chemical analysis apparatus for analysis of product gases. Reaction gases can enter through gas inlet tube 19 in electrode 12 with the same or different gas entering through swirl tubes 17 and 18, such as a carrier gas through the swirl tubes. Reaction gases also can enter only through swirl tubes 17 and 18 with gas inlet tube 19 closed by valve 20. By this means, the swirl number, a measure of extent of swirl, and the quantity of gases or vapor passing through the apparatus can be independently controlled.

Initiation of the discharge was easily accomplished in either air or nitrogen at pressures below about 0.1 atmosphere obtained by activating a vacuum pump attached to vacuum tube 23 with valve 24 opened with the other valves closed. After ignition of the discharge, operation at atmospheric pressure was accomplished by steadily increasing the chamber pressure by closing valve 24 connecting the chamber to the vacuum pump and then, as one atmosphere pressure was approached, opening valve 22 which allowed discharge gases to vent to atmospheric pressure. The chamber operated at a little over one atmosphere pressure due to pressure losses in the gas outlet tube 21. When using hydrocarbon gas, such as methane or natural gas flows, a nitrogen discharge was first initiated, to avoid combustion in the chamber, which was brought up to atmospheric pressure prior to addition of the hydrocarbon gas. The hydrocarbon gas to be reacted was then added to the chamber at steadily increasing rates and the nitrogen flow proportionately decreased until it was turned off.

Figure 2:
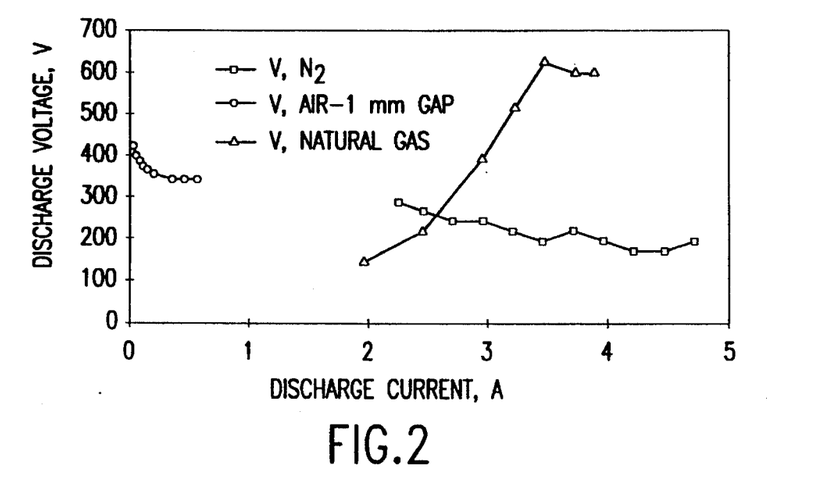
FIG. 2 is a plot of discharge voltage versus discharge current with the flow of air and natural gas through the glow discharge chamber shown in FIG. 1.

Using no flow of air at atmospheric pressure and an electrode separation of 1 mm, with one flat and one ported electrode, without ring 16, a discharge current and discharge voltage curve, as shown in FIG. 2, showed, typical for glow discharge, no change in voltage with increasing low current up to about 1 Amp. with relatively high voltages in excess of 350 volts. Varying pressure between 100 and 760 Torr changed the discharge voltage only slightly, but did reduce the maximum discharge current with increasing pressure. Thus, it was clear that the discharge was a glow, as compared to an arc, which is typically tens of amperes with low voltages of about 10 to 20 volts.

The current-voltage curve for a swirl stabilized atmospheric pressure nitrogen glow discharge obtained in the apparatus shown in FIG. 1 with electrode separation of 10 mm is shown in FIG. 2. The curves for air at 1 mm electrode spacing and nitrogen at 10 mm electrode spacing are qualitatively similar with the maximum current for the nitrogen swirl stabilized discharge greatly increased. The corresponding curve for a swirl stabilized natural gas glow discharge conducted under the same conditions is also shown in FIG. 2. This shows the rising portion of the curve with the natural gas glow discharge producing the normal glow current-voltage curve after the current exceeded 3.5 amperes. The maximum electric power supplied was on the order of 2.3 kW.

Chemical conversion efficiencies were measured by injecting gas samples into a Hewlett-Packard Model 5830A gas chromatograph. Some conversion in M. G. Industries CP grade methane was observed prior to introduction of methane swirl into the chamber. Results on back to back samples of product gas taken from swirl stabilized natural gas (Linde) glow discharge conducted at atmospheric pressure between electrodes 10 mm apart showed the product gas contained 14.6 and 14.9 percent acetylene. Concentrations of acetylene, ethylene and ethane in the input natural gas were found to be less than 0.8 percent by gas chromatography. Therefore, the acetylene in the product gas represented a conversion of more than 25 percent of the methane in the natural gas into acetylene. If only the case of methane conversion to acetylene and hydrogen is considered, the composition for the lower of the above two outputs is 10% acetylene, 31% hydrogen and 59% methane which represents 40% of the maximum possible conversion concentration of 25% obtainable by stoichiometric considerations. Under more optimum conditions, the amount of methane conversion to acetylene may be higher. The lower concentration of acetylene is due to dilution with the hydrogen produced. In these runs, the natural gas flow was 0.139 l/sec (8.3 l/min.) at 250 V and 3 A. The power input was about ⅓ of the maximum shown in FIG. 2. The 750 W of power consumed is consistent with the chemical equation for conversion of methane to acetylene and hydrogen and the measured acetylene concentrations at the above gas flow rate. Based on the 25 percent conversion of methane and an input of 750 W, the power conversion to chemical change efficiency is slightly over 50 percent. This shows the very high energy transfer in the atmospheric glow discharge between two electrodes spaced at 10 mm apart.

Figure 4:
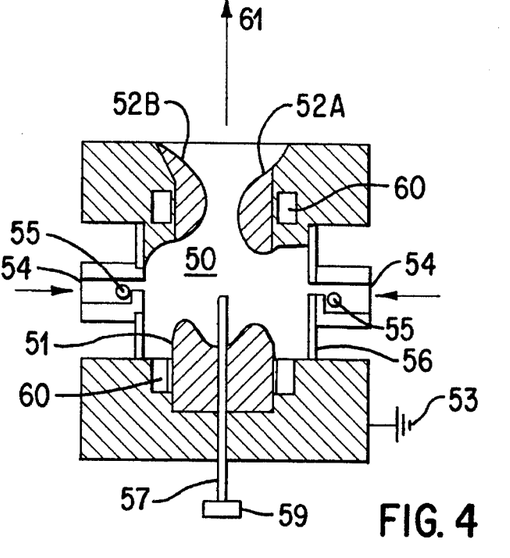
FIG. 4 is a cross-sectional schematic view of another embodiment of a glow discharge chamber according to this invention.

FIG. 4 schematically shows discharge chamber 50 with quartz walls 56. Electrode 51 has a concave surface opposing the exit port and is grounded to ground 53. The opposing electrode is shown as 52A on one side and 52B on the opposite side of the exit port to illustrate different suitable electrode shapes to define the exit port. It is desired that the electrode faces defining the exit port be curved to shape the gas flow path. Also, the curvature on the exit port, both the upstream and downstream portions, can modify the point of attachment of the discharge which changes the shape and character of the discharge in the chamber. The electrode forming the exit port is maintained at the desired potential differential from electrode 51 to maintain the gas glow discharge. The electrodes may be cooled, such as by circulation of gas or liquid through electrode cooling conduits 60. Gas is introduced into discharge chamber 50 through gas inlet channels 54 and swirl tubes 55 to create the desired gas swirl in discharge chamber 50. The exit of product gas is indicated by arrow 61. The gas glow discharge may be ignited by retractable ignition wire 57 positioned in desired ignition position by wire positioning means 59 and following ignition retracted through electrode 51.

Figure 5:
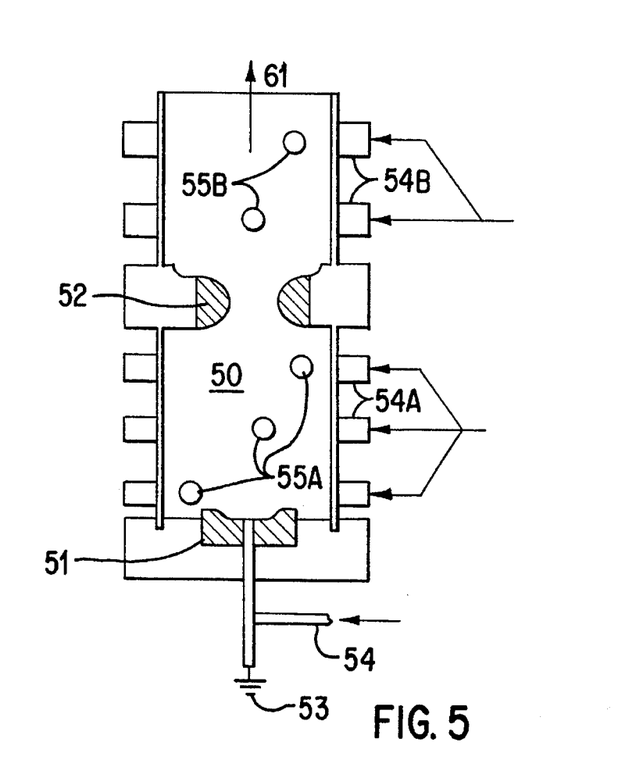
FIG. 5 is a cross-sectional schematic view of another embodiment of a glow discharge chamber according to this invention.

FIG. 5 schematically shows another configuration for discharge chamber 50 and electrodes 51 and 52. Electrode 52 forms the exit port from glow discharge chamber 50. Gas enters glow discharge chamber 50 through gas inlet channel 54 through the central portion of electrode 51 and through gas inlet channels 54A and swirl tubes 55A upstream from the exit port and through gas inlet channels 54B and swirl tubes 55B downstream of the exit port from glow discharge chamber 50. Gas injection means, not shown, may introduce the same or different gases into these gas inlet channels, such as fuel, oxidizing, reactant and/or non-reacting carrier or shield gases.

Figure 6:
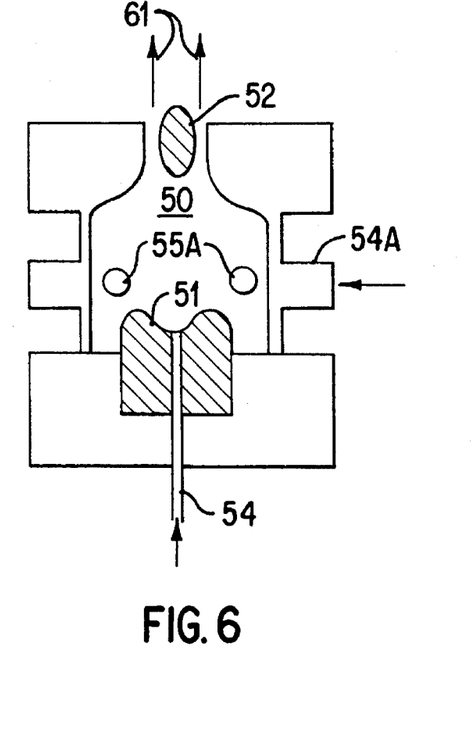
FIG. 6 is a cross-sectional schematic view of another embodiment of a glow discharge chamber according to this invention.

FIG. 6 schematically shows another embodiment of this invention wherein electrode 51 has a concave surface and opposing electrode 52 is in the central portion of the exit port forming an annular exit port for product gas 61 flowing from glow discharge chamber 50. Gas inlet channel 54 admits gas through electrode 51 and gas inlet channels 54A with swirl tubes 55A introduce additional gas, which may be the same or different from gas admitted through gas inlet channel 54, to glow discharge chamber 50.

Figure 7:
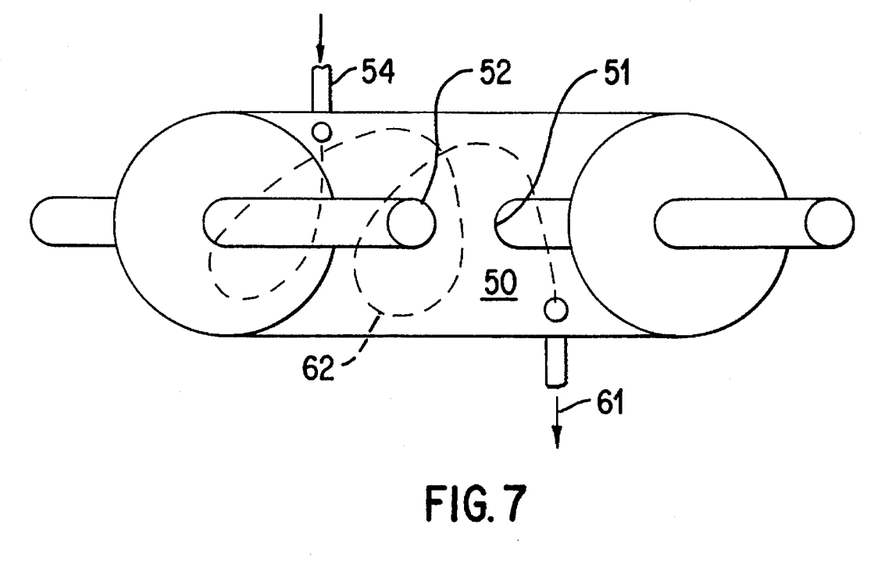
FIG. 7 is a schematic partially cut-away perspective view of another embodiment of a glow discharge chamber according to this invention.

FIG. 7 schematically shows another embodiment of the apparatus of this invention with cylindrical gas glow discharge chamber 50 and electrodes 51 and 52. Gas is passed through gas inlet channel 54 and passes through gas glow discharge chamber 50 in the swirling path shown as 62 and exits chamber 50 through an exit port as product gas 61.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. An apparatus for gas glow discharge comprising: opposing electrodes spaced greater than 3 mm apart within a glow discharge chamber, means for passing gas or vapor in a swirling pathway to form a vortex between said electrodes, means for maintaining an electrical potential differential between said electrodes to maintain a glow discharge between said electrodes, and exit port means in or near one of said electrodes.

2. An apparatus for gas glow discharge according to claim 1 wherein said exit port is in a central portion of one of said electrodes.

3. An apparatus for gas glow discharge according to claim 1 wherein both said electrodes are flat.

4. An apparatus for gas glow discharge according to claim 1 wherein one of said electrodes is an electrode opposing said exit port has a ring structure aligned with said exit port.

5. An apparatus for gas glow discharge according to claim 1 wherein one of said electrodes is a generally conical shaped electrode opposing said exit port and extending to a lower portion of said chamber.

6. An apparatus for gas glow discharge according to claim 1 wherein one of said electrodes has a concave face opposing said exit port.

7. An apparatus for gas glow discharge according to claim 1 wherein said opposing electrodes are spaced about 3 to about 200 mm apart.

8. An apparatus for gas glow discharge according to claim 1 wherein said opposing electrodes are spaced about 5 to about 25 mm apart.

9. An apparatus for gas glow discharge according to claim 1 comprising a vacuum pump which maintains said glow discharge chamber at a pressure of about 0.5 to about 10 atmospheres.

10. An apparatus for gas glow discharge according to claim 1 comprising a vacuum pump which maintains said glow discharge chamber at about atmospheric pressure.

11. An apparatus for gas glow discharge according to claim 1 comprising at least one valve which maintains gas flow through said glow discharge at a velocity of about 0.1 to about 10,000 meters per second.

12. An apparatus for gas glow discharge according to claim 1 comprising a vacuum pump which maintains subatmospheric pressure during ignition of said discharge and then increases pressure to a higher operating pressure following said ignition.

13. An apparatus for gas glow discharge according to claim 1 comprising electrode positioning means which move said electrodes close together to an ignition position while applying an ignition voltage and then move said electrodes apart increasing spacing between them to an operating position following said ignition.

14. An apparatus for gas glow discharge according to claim 1 comprising an ignition electrode and means for applying a voltage to said ignition electrode during an ignition stage.

15. An apparatus for gas glow discharge according to claim 14 comprising ignition electrode positioning means which move said ignition electrode to an ignition position while applying said voltage and then move said ignition electrode to an operating position following said ignition.

16. An apparatus for gas glow discharge according to claim 1 wherein said exit port is an annular opening in one of said electrodes.

17. An apparatus for gas glow discharge according to claim 1 additionally comprising burner means downstream of said exit port means for combustion of gases passing from said exit port means.

18. An apparatus for gas glow discharge according to claim 1 comprising duct means downstream of said exit port means for conduct of product gases passing from said exit port means for further use.

19. An apparatus for gas glow discharge according to claim 18 comprising injection means which inject at least one gas into said duct means.

20. An apparatus for gas glow discharge according to claim 1 comprising injection means which inject at least one gas into said glow discharge chamber.

21. An apparatus for gas glow discharge according to claim 1 wherein said glow discharge chamber has at least a portion open to the atmosphere.

22. An apparatus for gas glow discharge according to claim 1 wherein one of said electrodes defines a gas inlet port.

23. An apparatus for gas glow discharge comprising: opposing electrodes spaced about 3 to about 200 mm apart within a glow discharge chamber, means for passing gas or vapor in a swirling pathway through said gas glow discharge at a velocity of about 0.1 to about 10,000 meters per second to form a vortex between said electrodes, means which maintain said gas glow discharge chamber at a pressure of about 0.5 to about 10 atmospheres, means for maintaining an electrical potential differential between said electrodes to maintain said glow discharge between said electrodes, ignition means for igniting said gas glow discharge, and exit port means in or near one of said electrodes for exit of product gas from said gas glow discharge chamber.

\* \* \* \* \*